United States Patent
Yatabe et al.

(10) Patent No.: US 7,435,239 B2
(45) Date of Patent: Oct. 14, 2008

(54) INJECTION NEEDLE WITH NEEDLE POINT OFFSET FROM CENTRAL PLANE

(75) Inventors: Teruyuki Yatabe, Yamanashi (JP); Tetsuya Ooyauchi, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 10/509,657

(22) PCT Filed: Mar. 27, 2003

(86) PCT No.: PCT/JP03/03872

§ 371 (c)(1),
(2), (4) Date: Sep. 29, 2004

(87) PCT Pub. No.: WO03/082384

PCT Pub. Date: Oct. 9, 2003

(65) Prior Publication Data

US 2005/0107751 A1    May 19, 2005

(30) Foreign Application Priority Data

Mar. 27, 2003  (JP) .............................. 2002-097015

(51) Int. Cl.
*A61M 5/32* (2006.01)
(52) U.S. Cl. ...................................................... 604/272

(58) Field of Classification Search ................. 604/272, 604/273, 274, 171, 6.05, 6.06, 110, 187; 112/49
See application file for complete search history.

(56) References Cited

U.S. PATENT DOCUMENTS

| | | | | |
|---|---|---|---|---|
| 3,071,135 A | * | 1/1963 | Baldwin et al. | 604/274 |
| 3,308,822 A | * | 3/1967 | De Luca | 604/274 |
| 3,448,740 A | * | 6/1969 | Figge | 604/274 |
| 4,128,351 A | * | 12/1978 | Kurtz et al. | 606/223 |
| 5,064,411 A | * | 11/1991 | Gordon, III | 604/272 |
| 5,752,942 A | * | 5/1998 | Doyle et al. | 604/274 |
| 5,968,022 A | * | 10/1999 | Saito | 604/272 |
| 6,517,523 B1 | * | 2/2003 | Kaneko et al. | 604/272 |
| 7,070,583 B1 | * | 7/2006 | Higuchi et al. | 604/274 |

FOREIGN PATENT DOCUMENTS

| | | |
|---|---|---|
| JP | 8-187287 A | 7/1996 |
| JP | 2000-262615 A | 9/2000 |
| JP | 2001-309977 A | 11/2001 |

* cited by examiner

*Primary Examiner*—Kevin C. Sirmons
*Assistant Examiner*—Catherine N Witczak
(74) *Attorney, Agent, or Firm*—Buchanan Ingersoll & Rooney PC

(57) ABSTRACT

An injection needle that can reduce the pain associated with piercing a patient's skin with a needle. The needle has a needle tip provided by forming at least two or more ground surfaces after a first ground surface is formed at the tip of a needle tube. The needle tip is not present on a central plane, which is the plane that crosses vertically the first ground surface and includes a central axis of the needle tube.

17 Claims, 8 Drawing Sheets

(b)     (a)     (c)

(b)      (a)      (c)

(b)  (a)  (c)

INJECTION NEEDLE WITH NEEDLE POINT OFFSET FROM CENTRAL PLANE

TECHNICAL FIELD

The present invention relates to an injection needle for medical use, and more particularly to an injection needle having a small diameter for use in self-injection.

BACKGROUND ART

Injection needles for medical use generally have an edge surface with two slant angles as viewed in side elevation, which is generally called a lancet point. FIG. 7 is a plan view of the edge surface of a lancet point structure of a conventional injection needle. In FIG. 7, it is assumed that the injection needle has a needle point at a distal end thereof and an opposite end at a proximal end thereof. The injection needle 11 has a needle tube 12 including an edge surface 13 disposed on the distal end. The edge surface 13 includes a first ground facet 13a formed closer to the proximal end, and a second ground facet 13b and a third ground facet 13c that are formed closer to the distal end than the first ground facet 13a. The second ground facet 13b and the third ground facet 13c are symmetrical in shape with respect to the major axis of the edge surface that is of a substantially elliptical shape. The sharp needle point 15 on the distal end of the edge surface 13 is present on a central plane 16 that crosses the first ground facet 13a perpendicularly and includes the central axis of the needle tube 12.

FIGS. 8(a) through 8(c) are views illustrative of a process of forming the edge surface 13 of the lancet point structure, and show in side elevation the injection needle 11 in the vicinity of its distal end illustrated in FIG. 7. For forming the edge surface 13 of the lancet point structure, as shown in FIG. 8(a), a grinding wheel is applied to the distal end portion of the needle tube 12, which is in the form of a hollow tube, at an angle $\alpha$ ($0° < \alpha < 90°$) with respect to the central axis 18 of the needle tube 12, and grinds the distal end portion to form the first ground facet 13a whose angle with respect to the central axis 18 of the needle tube 12 is $\alpha$.

Then, as shown in FIG. 8(b), the needle tube 12 is turned a certain angle about the central axis 18 toward the viewer of FIG. 8(b). The grinding wheel is applied to the distal end portion of the needle tube 12 at an angle $\phi$ ($0° < \alpha < \phi < 90°$) with respect to the first ground facet 13a around the central axis 18 of the needle tube 12, and grinds the distal end portion to form the second ground facet 13b whose angle with respect to the central axis 18 of the needle tube 12 is $\phi$.

Thereafter, as shown in FIG. 8(c), the needle tube 12 is turned about the central axis 18 from the state shown in FIG. 8(a) away from the viewer of FIG. 8(b). The grinding wheel is applied to the distal end portion of the needle tube 12 at an angle $\theta$ ($0° < \alpha < \theta = \phi < 90°$), which is equal to the angle $\phi$, with respect to the first ground facet 13a around the central axis 18 of the needle tube 12, and grinds the distal end portion to form the third ground facet 13c whose angle with respect to the central axis 18 of the needle tube 12 is $\theta$ ($=\phi$). The angle through which the needle tube 12 is turned toward the viewer of FIG. 8(b) is equal to the angle through which the needle tube 12 is turned toward the viewer of FIG. 8(c). In this manner, as shown in FIG. 7, the second ground facet 13b and the third ground facet 13c are symmetrical in shape with respect to the major axis of the edge surface which is of a substantially elliptical shape.

The injection needle 11 having the edge surface 13 of the conventional lancet point structure can easily pierce a skin 7 as the force required to penetrate the skin 7 is small, and poses a reduced burden on the patient. However, inasmuch as the edge surface 13 is of a symmetrical shape, when the needle 11 pierces the skin, or more specifically, when the injection needle 11 pierces a skin 7 perpendicularly thereto for insulin injection by way of self-injection, the sharp needle point 15 on the distal end of the edge surface 13 first makes point-to-point contact with the skin 7, often causing sharp pain. The puncture pain is sustained until the edge surface 13 goes fully through the skin 7. In the present specification, the pain caused when the distal end of the edge surface 13 contacts the skin 7 and the edge surface 13 is further forced into the skin 7 is referred to as "puncture pain".

In view of the above conventional problems, it is therefore an object of the present invention to provide an injection needle which is capable of reducing puncture pain caused when the injection needle penetrates the skin.

DISCLOSURE OF INVENTION

The above object can be accomplished by the present invention as follows:

(1) According to the present invention, an injection needle having a first ground facet formed on a distal end of a needle tube and at least two ground facets subsequently formed to provide a needle point is characterized in that a plane which crosses the first ground facet perpendicularly thereto and includes a central axis of the needle tube is regarded as a central plane, and the needle point is not present on the central plane.

(2) According to the present invention, in the injection needle described above in (1), the minimum distance between the needle point and the central plane is in the range from 3 to 20% of the maximum outside diameter of the first ground facet in the direction of a minor axis thereof.

(3) According to the present invention, in the injection needle described above in (1), the minimum distance between the needle point and the central plane is in the range from 8 to 100 μm.

(4) According to the present invention, an injection needle having an edge surface including three ground facets formed on a distal end of a needle tube to provide a needle point is characterized in that one of the ground facets which is remotest from the needle point is regarded as a first ground facet, and the other ground facets as a second ground facet and a third ground facet; and an angle $\alpha$ between the first ground facet and a central axis of the needle point, an angle $\phi$ between the second ground facet and the central axis of the needle point, and an angle $\theta$ between the third ground facet and the central axis of the needle point are related to each other by: $\alpha<\phi, \alpha<\theta$, and $\phi \neq \theta$.

(5) According to the present invention, in the injection needle described above in (4), a plane which crosses the first ground facet perpendicularly thereto and includes the central axis of the needle tube is regarded as a central plane; and the minimum distance between the needle point and the central plane is in the range from 3 to 20% of the maximum outside diameter of the edge surface in the direction of a minor axis thereof.

(6) According to the present invention, in the injection needle described above in (4), the minimum distance between the needle point and the central plane is in the range from 8 to 100 μm.

(7) According to the present invention, in the injection needle described above in (4) through (6), the length of the second ground facet in the direction of the central axis and the length of the third ground facet in the direction of the central axis are in the range from 20 to 80% of the whole length of the ground facets in the direction of the central axis.

(8) According to the present invention, in the injection needle described above in (1) through (7), when the injection needle pierces a silicone rubber sheet having a thickness of 0.5 mm at a penetration speed of 10 mm/min., an initial value of the load with respect to a penetration distance is 6 gf/mm or less.

The injection needle according to the present invention is capable of effectively distributing forces that are applied from the edge surface to the skin when the edge surface is brought into contact with the skin from its distal end and further forced into the skin. Therefore, the puncture pain that is caused when the injection needle pierces the skin can be reduced.

BEST MODE FOR CARRYING OUT THE INVENTION

Figure 1:
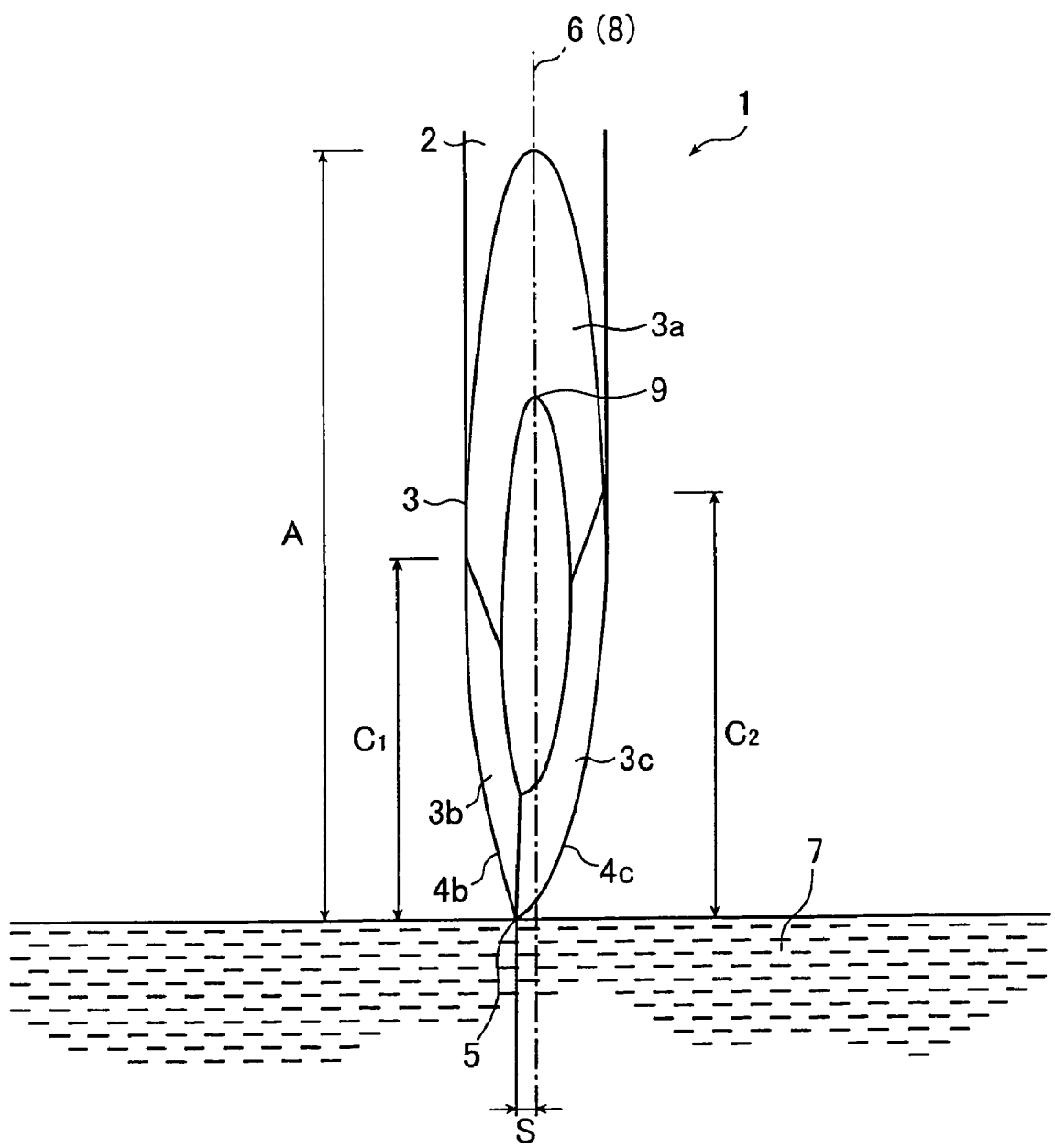
FIG. 1 is a plan view showing an edge surface portion of an injection needle according to an embodiment of the present invention.

FIG. 1 is a plan view showing an edge surface portion of an injection needle according to an embodiment of the present invention. In FIG. 1, it is assumed that the injection needle has a needle point at a distal end thereof and an opposite end at a proximal end thereof. The injection needle 1 according to the present invention has a needle tube 2 including an edge surface 3 disposed on the distal end. The edge surface 3 includes a first ground facet 3a positioned closer to the proximal end and remotest from a needle point 5, and two ground facets, i.e., a second ground facet 3b and a third ground facet 3c, positioned closer to the distal end than the first ground facet 3a. Thus, the injection needle 1 according to the present invention has the edge surface 3 that is of a structure similar to an edge surface of the conventional lancet point structure. Therefore, the edge surface 3 can be formed in the same manner as an edge surface of the conventional lancet point structure. Specifically, the distal end portion of the needle tube 2 is ground at a certain angle α with respect to the central axis 8 of the needle tube 2, forming the first ground facet 3a. Then, the needle tube 2 is turned about the central axis 8 through angles, and the first ground facet 3a, which is of a substantially elliptical shape, is ground on different sides of the major axis thereof at angles φ, θ greater than the angle α, forming the second ground facet 3b and the third ground facet 3c. The injection needle 1 according to the present invention is formed such that the needle point 5 is not present on a central plane 6 that crosses the first ground facet 3a perpendicularly and includes the central axis of the needle tube 2. Stated otherwise, the injection needle 1 according to the present invention is formed such that the needle point 5 positioned on the distal end of the edge surface 3 is not present on the major axis of the substantially elliptical shape of the first ground facet 3a when it is first formed.

The injection needle 1 according to the present invention is characterized in that the needle point 5 is not present on the central plane 6 that crosses the first ground facet 3a perpendicularly and includes the central axis of the needle tube 2 (also referred to simply as "central plane 6"). Of edges 4b, 4c provided by the second ground facet 3b and the third ground facet 3c, either one (in FIG. 1, the edge 4c provided by the third ground facet 3c) projects toward the distal end of the edge surface 3. Since the injection needle 1 according to the present invention has its edge surface 3 thus constructed, when the injection needle 1 pierces a skin 7, the injection needle 1 first contacts the skin 7 not by way of point-to-point contact between the skin 7 and the sharp needle point 5, but by way of more linear contact between the skin 7 and a needle region including the needle point 5 and a portion of the curved edge 4b or 4c projecting toward the distal end of the edge surface 3 (a contact portion has a linear shape). Accordingly, when the distal end of the edge surface 3 contacts the skin 7 and the edge surface 3 is further forced into the skin 7, forces that are applied from the edge surface 3 to the skin 7 are distributed. As a result, the puncture pain caused when the injection needle 1 penetrates the skin 7 can be reduced.

The injection needle 1 according to the present invention may be arranged such that when the injection needle 1 penetrates the skin 7, the needle point 5 may not make initial contact with the skin 7, but only the portion of the curved edge 4b or 4c projecting toward the distal end of the edge surface 3 may contact the skin 7 such that a contact portion has a linear shape. In this case, the puncture pain caused when the injection needle 1 penetrates the skin 7 can also be reduced. The direction in which the edge 4b or 4c projects is not limited in particular, but may be the direction of the second ground facet 3b, i.e., the edge 4b may project. That is, the needle point 5 may be positioned on either side of the central plane 6.

With the injection needle 1 according to the present invention, since the needle point 5 is not on the central plane 6 as shown in FIG. 1, the needle point 5 is spaced a distance from the central plane 6. The minimum distance S between the needle point 5 and the central plane 6 should preferably be in the range of 3 to 20% of the maximum outside diameter of the first ground facet 3a in the direction of the minor axis of the substantially elliptical shape of the first ground facet 3a that is initially formed, and more preferably in the range of 5 to 15% of the maximum outside diameter. As described later on, since the injection needle 1 according to the present invention should preferably be used as an injection needle having a small diameter for use in insulin injection and self-injection, with the outside diameter of 0.36 mm or less, the minimum distance between the needle point 5 and the central plane 6 should preferably be in the range from 8 to 100 μm and more preferably in the range from 8 to 35 μm.

With the minimum distance S between the needle point 5 and the central plane 6 being in the above range, since the portion of the edge surface 3 which makes initial contact with the skin 7 is of a more linear shape, when the edge surface 3 is brought into contact with the skin 7 from the distal end thereof and forced into the skin 7, forces that are applied from the edge surface 3 to the skin 7 are sufficiently distributed, thus reducing the puncture pain. With the minimum distance S between the needle point 5 and the central plane 6 being in the above range, furthermore, the portions of the edges 4b, 4c which project toward the distal end of the edge surface 3 and will make initial contact with the skin 7 are not too large, so that when the edge surface 3 is further forced into the skin 7, the penetration of the skin by the edge surface 3 is not obstructed, and the puncture pain is not increased.

Figure 2:
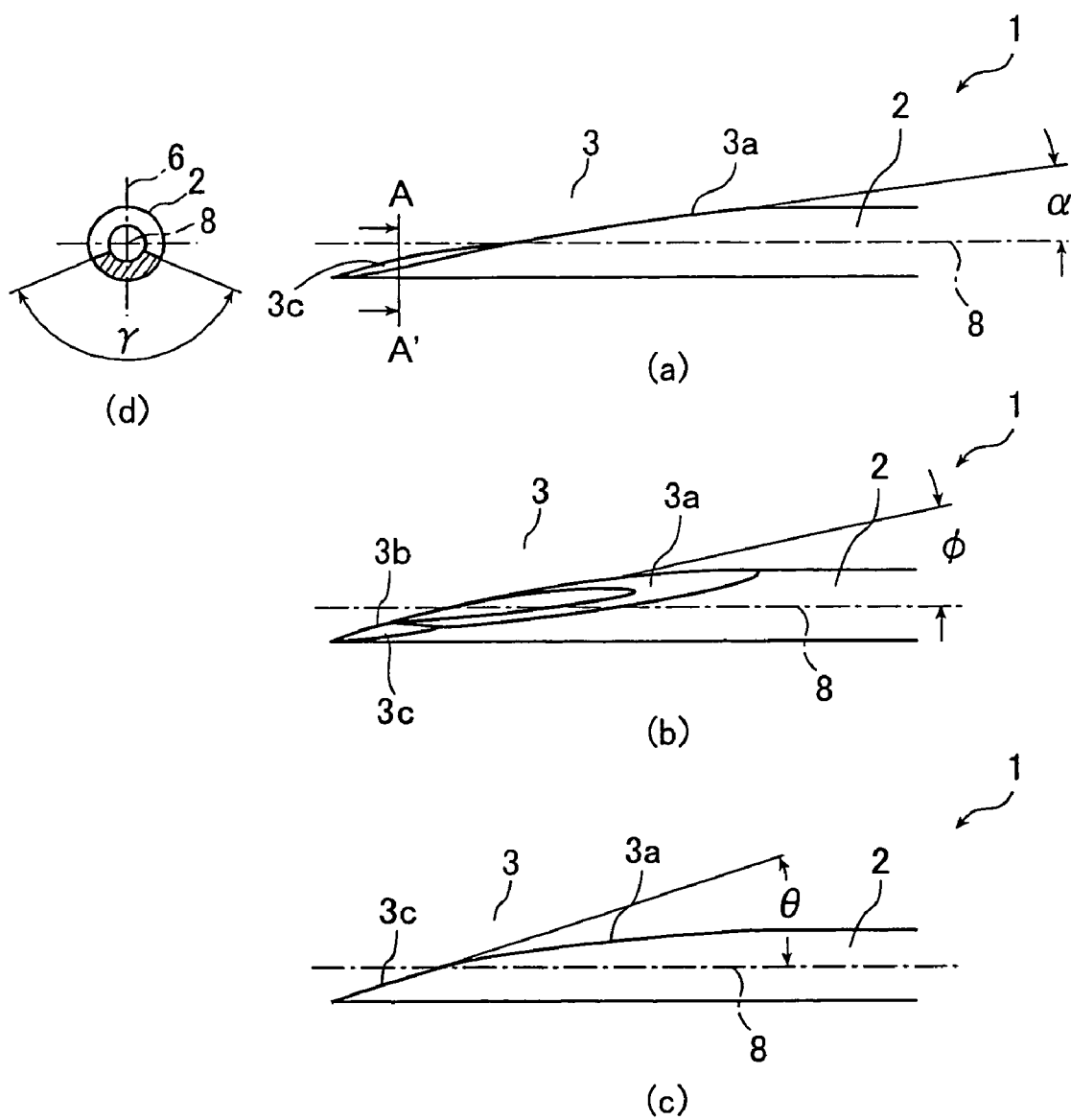
FIGS. 2(a) through 2(c) are side elevational views of the injection needle in the vicinity of its distal end illustrated in FIG. 1, FIG. 2(a) being a side elevational view of the injection needle with a first ground facet 3a being viewed flush with line of sight, FIG. 2(b) being a side elevational view of the injection needle with a second ground facet 3b being viewed flush with line of sight, FIG. 2(c) being a side elevational view of the injection needle with a third ground facet 3c being viewed flush with line of sight, and FIG. 2(d) being a cross-sectional view taken along line A-A' of FIG. 2(a)

The injection needle according to the present invention will further be described with reference to FIG. 2. FIGS. 2(a) through 2(c) are side elevational views of the injection needle 1 in the vicinity of its distal end illustrated in FIG. 1. FIG. 2(a) is a side elevational view of the injection needle with a first ground facet 3a being viewed flush with line of sight, FIG. 2(b) is a side elevational view of the injection needle with a second ground facet 3b being viewed flush with line of sight, and FIG. 2(c) is a side elevational view of the injection needle with a third ground facet 3c being viewed flush with line of sight. FIG. 2(d) is a cross-sectional view taken along line A-A' of FIG. 2(a). In FIG. 2(d), the angle γ is an angle formed between the second ground facet 3b and the third ground facet 3c in a cross section that is perpendicular to the central axis 8 of the injection needle 1.

As shown in FIG. 2(a), the first ground facet 3a has an angle α with respect to the central axis 8 of the needle tube 2. As shown in FIG. 2(b), the second ground facet 3b has an angle φ with respect to the central axis 8 of the needle tube 2. As shown in FIG. 2(c), the third ground facet 3c has an angle θ with respect to the central axis 8 of the needle tube 2. On the injection needle 1 according to the present invention, these angles α, φ, and θ have the following relationship:

$$0°<\alpha<\phi\neq\theta<90°$$

The angle of the second ground facet 3b (φ) and the third ground facet 3c (θ) with respect to the central axis 8 of the needle tube 2 is greater than the angle of the first ground facet 3a (α) similarly to the edge surface of the conventional lancet point structure. The injection needle 1 according to the present invention is characterized in that the angle φ and the angle θ are different from each other. As described above, with the injection needle 1 according to the present invention, after the first ground facet 3a having the angle α with respect to the central axis 8 of the needle tube 2 is formed on the distal end portion of the needle tube 2, the second ground facet 3b and the third ground facet 3c are formed on the different sides of the major axis of the first ground facet 3a which is of a substantially elliptical shape, respectively at the angle φ and the angle θ with respect to the central axis 8 of the needle tube 2. Therefore, if the angle φ and the angle θ are different from each other, then either one (the third ground facet 3c in FIG. 1) of the second ground facet 3b and the third ground facet 3c is formed so as to project beyond the central plane 6 toward the other ground facet. Consequently, either one (4c in FIG. 1) of the edges 4b, 4c provided by the second ground facet 3b and the third ground facet 3c is of a shape projecting toward the distal end of the edge surface 3. As described above, when the injection needle 1 pierces the skin 7, the injection needle 1 first contacts the skin 7 not by way of point-to-point contact between the skin 7 and the sharp needle point 5, but by way of more linear contact between the skin 7 and a needle region including the needle point 5 and a portion of the curved edge 4b or 4c projecting toward the distal end of the edge surface 3, or more linear contact between the skin 7 and a portion of the curved edge 4b or 4c projecting toward the distal end of the edge surface 3 (that is, a contact portion has a linear shape). Accordingly, when the distal end of the edge surface 3 contacts the skin 7 and the edge surface 3 is further forced into the skin 7, forces that are applied from the edge surface 3 to the skin 7 are sufficiently distributed, reducing the puncture pain.

With the injection needle 1 according to the present invention, as the second ground facet 3b and the third ground facet 3c is formed at the different angles φ, θ with respect to the central axis 8 of the needle tube 2, the second ground facet 3b and the third ground facet 3c have different sizes and shapes, and the length C1 of the second ground facet 3b and the length C2 of the third ground facet 3c in the direction of the central axis 8 of the needle tube 2 are different from each other, as shown in FIG. 1. C1 and C2 vary depending on the selection of the angles α, φ, and θ. With the injection needle 1 according to the present invention, it is preferable to set C1 and C2 to 20 through 80% of the length A of the entire edge surface 3 along the central axis 8. If C1 and C2 is in the above range, then the edges 4b, 4c provided by the second ground facet 3b and the third ground facet 3c have sizes large enough to cut the skin 7, allowing the injection needle 1 to penetrate the skin 7 easily. Since no sharp protrusion is formed inside a jaw 9, when the portion of the injection needle 1 near the jaw 9 goes through the skin 7, the patient is prevented from feeling a strong pain.

With the injection needle 1 according to the present invention, since the needle point 5 is not on the central plane 6, when the injection needle 1 pierces the skin 7, the injection needle 1 first contacts the skin 7 not by way of point-to-point contact between the skin 7 and the sharp needle point 5, but by way of more linear contact between the skin 7 and a needle region including the needle point 5 and a portion of the curved edge 4 projecting toward the distal end of the edge surface 3 or more linear contact between the skin 7 and a portion of the curved edge 4 projecting toward the distal end of the edge surface 3 (that is, a contact portion has a linear shape). Therefore, when the edge surface 3 is brought into contact with the skin 7 from its distal end and forced into the skin 7, forces that are applied from the edge surface 3 to the skin 7 are sufficiently distributed. Therefore, any increase in an initial load on the object that is pierced by the injection needle 1 according to the present invention is small. Specifically, when the injection needle 1 according to the present invention pierces a silicone rubber sheet having a thickness of 0.5 mm at a penetration speed of 10 mm/min., the initial value of the load with respect to the penetration distance should preferably be 6 gf/mm or less. Since the injection needle 1 according to the present invention should preferably be used as an injection needle for use in insulin injection and self-injection, the above numerical value is measured when the injection needle pierces the silicone rubber sheet perpendicularly thereto. This numerical value differs from silicone rubber to silicone rubber, but covers a wide range of silicone rubbers for medical use, e.g., for use in container plugs that are to be pierced by injection needles for extracting or injecting contents. In Examples to be described later, silicone rubber sheets having durometer hardness A50 (JIS-K6253) were used.

The injection needle 1 according to the present invention is similar to the conventional injection needle except that the edge surface 3 has the above structure. Therefore, the material and diameter of the needle tube 2 may be selected in the range of the conventional injection needle. The needle tube 2 may be made of an iron material including stainless steel, a non-ferrous metal material such as aluminum, copper, titanium, or the like, a heat-resistant material such as nickel, cobalt, or molybdenum, a metal having a low melting point such as lead or tin, a precious metal material such as gold, silver, or platinum, or an alloy thereof.

Inasmuch as the injection needle 1 according to the present invention is preferable as an injection needle for use in self-injection by the patient, such as insulin injection, the injection needle 1 should preferably have a small diameter. Specifically, the outside diameter of the needle tube 2 should preferably be 0.36 mm or less, or more preferably in the range from 0.18 to 0.30 mm. The inside diameter of the needle tube 2 should preferably be 0.19 mm or less, or more preferably in the range from 0.07 to 0.17 mm.

Figure 7:
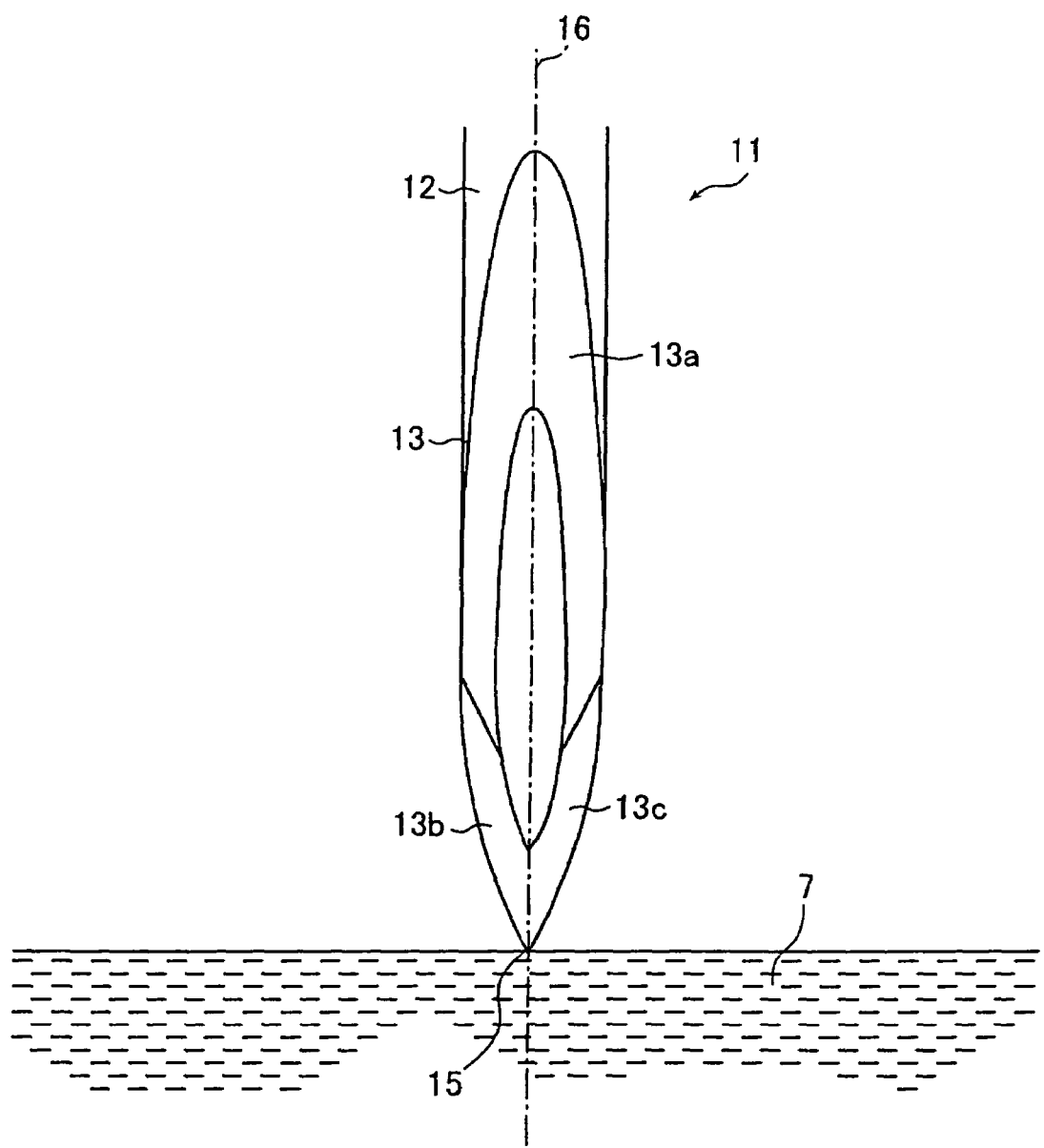
FIG. 7 is a plan view of an edge surface portion of a conventional injection needle.

As the injection needle for self-injection pierces the skin perpendicularly thereto, the distal end of the edge surface is brought into perpendicular contact with the skin. The conventional injection needle 11 having the sharp needle point 5 on the distal end of the edge surface 13 as shown in FIG. 7 causes a sharp puncture pain when the injection needle 11 pierces the skin 7 because the sharp needle point 5 makes point-to-point contact with the skin 7 when the injection needle 11 first contacts the skin 7. According to the present invention, however, as described above, the injection needle 1 first contacts the skin 7 by way of more linear contact between the skin 7 and a needle region including the needle point 5 and a portion of the curved edge 4b or 4c projecting toward the distal end of the edge surface 3, or more linear contact between the skin 7 and a portion of the curved edge 4b or 4c projecting toward the distal end of the edge surface 3 (that is, a contact portion has a linear shape). Accordingly, forces that are applied from the edge surface 3 to the skin 7 are effectively reduced, and the injection needle 1 is highly effective to reduce the puncture pain caused when the injection needle 1 pierces the skin 7.

The needle tube 2 as seen in side elevation may be shaped not only as a straight tube, but also as a tapered shape whose outside diameter decreases toward the distal end or the proximal end. The injection needle 1 having a tapered side-elevational shape may be either of a tapered shape in its entirety or of a tapered shape in part of the needle tube 2 or of a tapered shape in part of the edge surface 3. The injection needle 1 which is of a tapered shape in part of the edge surface 3 may be produced by forming the second ground facet 3b or the third ground facet 3c not in a single grinding process, but in a plurality of grinding processes performed at different angles with respect to the central axis 8. Specifically, the needle point 5 of the injection needle 1 according to the present invention may be produced by forming the first ground facet 3a and thereafter forming three or more ground facets.

EXAMPLES

Figure 3:
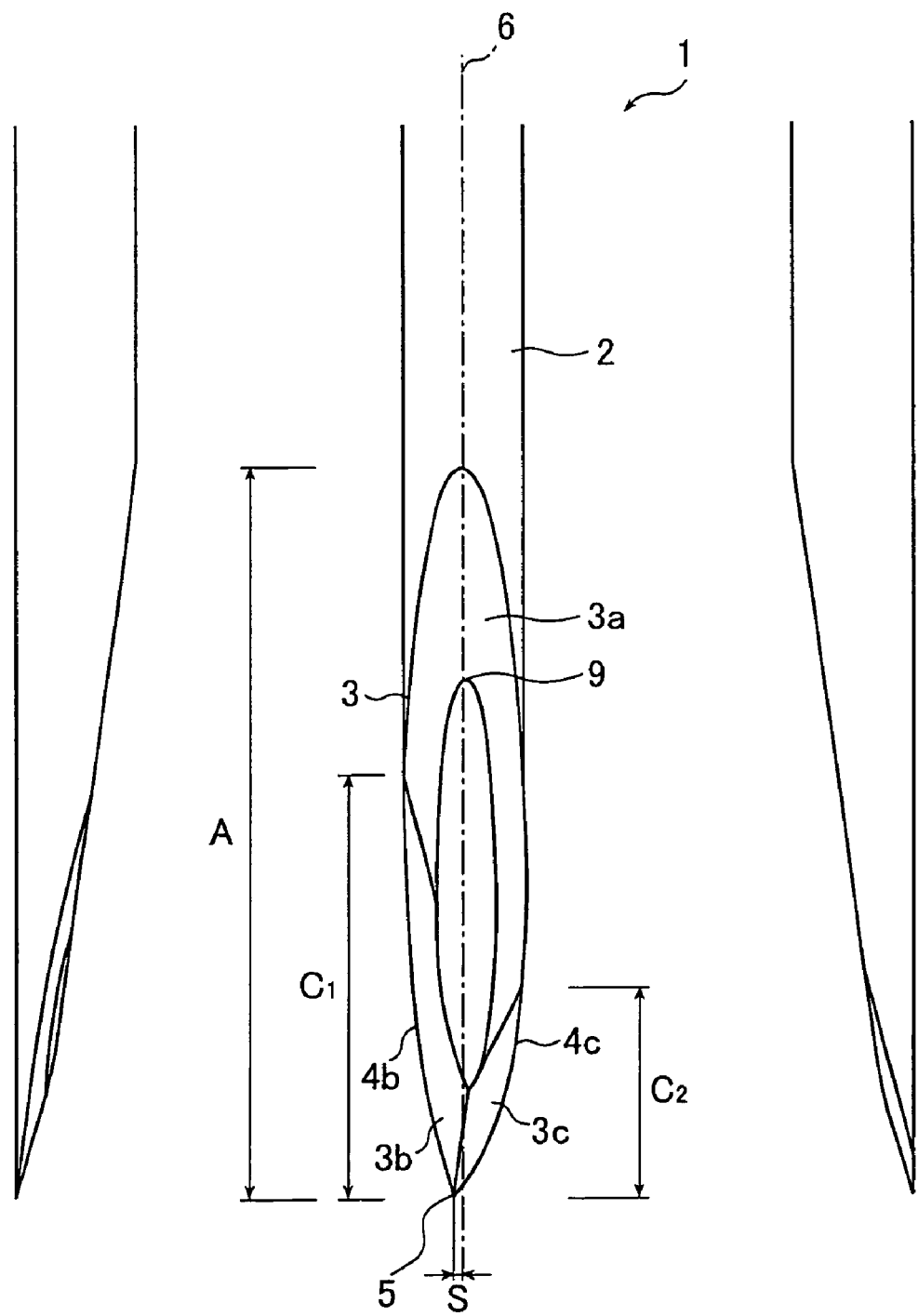
FIG. 3(a) is a plan view of an edge surface portion of an injection needle according to Inventive Example 1.
FIG. 3(b) is a left side elevational view of the injection needle 1 in the vicinity of its distal end illustrated in FIG. 3(a)
FIG. 3(c) is a right side elevational view of the injection needle 1 in the vicinity of its distal end illustrated in FIG. 3(a), FIGS. 3(b) and 3(c) being views of the injection needle with a first ground facet 3a being viewed flush with line of sight.
Figure 4:
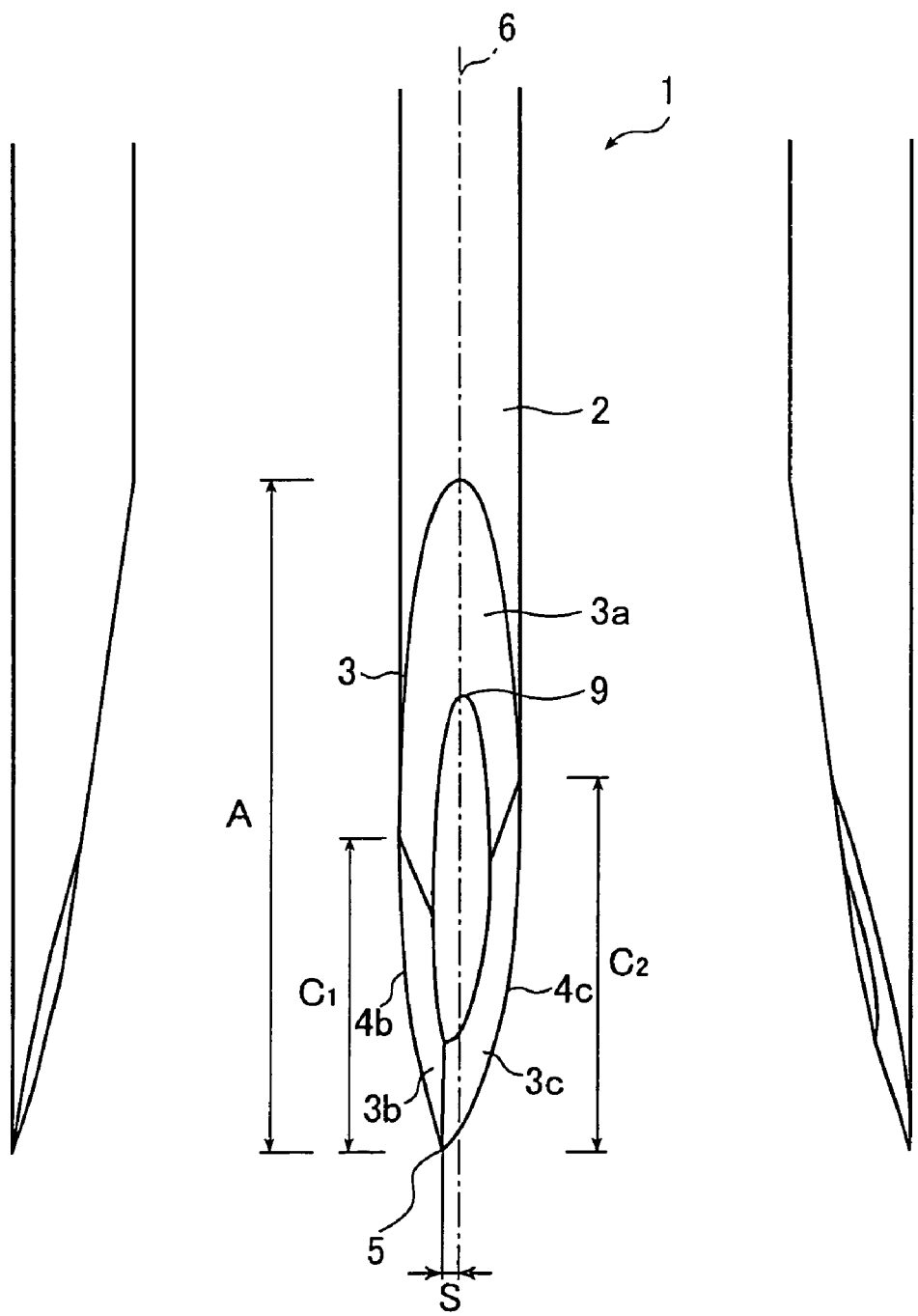
FIG. 4(a) is a plan view of an edge surface portion of an injection needle according to Inventive Example 2.
FIG. 4(b) is a left side elevational view of the injection needle 1 in the vicinity of its distal end illustrated in FIG. 4(a)
FIG. 4(c) is a right side elevational view of the injection needle 1 in the vicinity of its distal end illustrated in FIG. 4(a), FIGS. 4(b) and 4(c) being views of the injection needle with a first ground facet 3a being viewed flush with line of sight.
Figure 5:
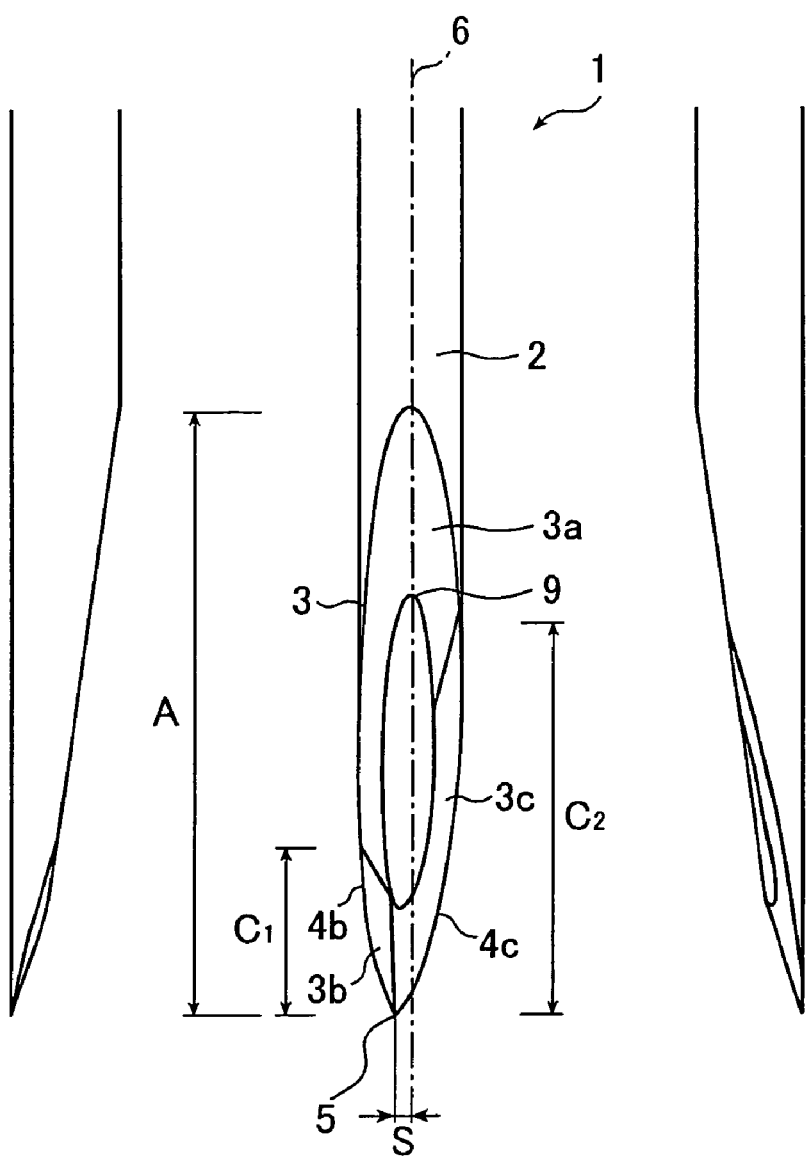
FIG. 5(a) is a plan view of an edge surface portion of an injection needle according to Inventive Example 3.
FIG. 5(b) is a left side elevational view of the injection needle 1 in the vicinity of its distal end illustrated in FIG. 5(a)
FIG. 5(c) is a right side elevational view of the injection needle 1 in the vicinity of its distal end illustrated in FIG. 5(a), FIGS. 5(b) and 5(c) being views of the injection needle with a first ground facet 3a being viewed flush with line of sight.
Figure 8:
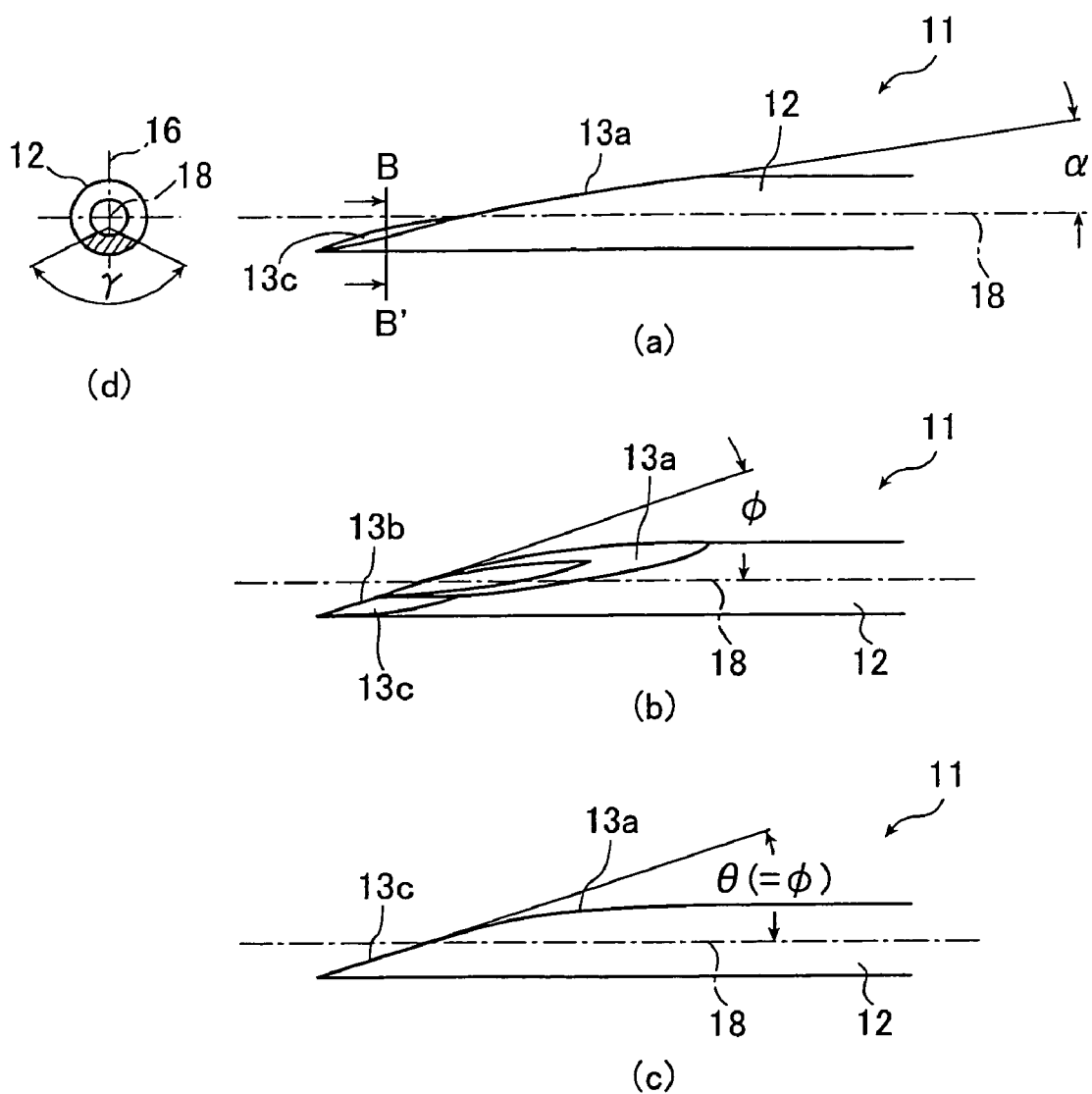
FIGS. 8(a) through 8(c) are side elevational views of the injection needle 11 in the vicinity of its distal end illustrated in FIG. 7, FIG. 8(a) being a side elevational view of the injection needle with a first ground facet 13a being viewed flush with line of sight, FIG. 8(b) being a side elevational view of the injection needle with a second ground facet 13b being viewed flush with line of sight, FIG. 8(c) being a side elevational view of the injection needle with a third ground facet 13c being viewed flush with line of sight, and FIG. 8(d) being a cross-sectional view taken along line B-B' of FIG. 8(a).

The distal end of a hollow tube (needle tube) of stainless steel having an outside diameter of 0.2 mm and an inside diameter of 0.1 mm was ground according to the above procedure to produce an injection needle according to Inventive Example 1 having the edge surface 3 shown in FIG. 3. The angles and dimensions of various regions of the injection needle according to Inventive Example 1 are shown in Table 1. In Table 1, γ represents an angle formed between the second ground facet and the third ground facet in a cross section that is perpendicular to the central axis of the injection needle, as shown in FIG. 2(d). Similarly, an injection needle according to Inventive Example 2 having an edge surface shown in FIG. 4 and an injection needle according to Inventive Example 3 having an edge surface shown in FIG. 5 were produced. Comparative Examples 1 through 6 are conventional injection needles 11 of stainless steel, as shown in FIGS. 7 and 8, where the angle φ of the second ground facet 13b with respect to the central axis 18 of the needle tube 12 and the angle θ of the third ground facet 13c with respect to the central axis 18 of the needle tube 12 are equal to each other. In FIG. 7, the reference numeral 16 corresponds to the reference numeral 6 in FIG. 1. FIG. 8(d) is a cross-sectional view taken along line B-B' of FIG. 8(a). In FIG. 8(d), the angle γ corresponds to the angle γ in FIG. 2(d).

TABLE 1

Edge surface shapes of injection needles according to Inventive Examples

|  | Inventive Example | | |
| --- | --- | --- | --- |
|  | 1 | 2 | 3 |
| Outside diameter (mm) | 0.2 | 0.2 | 0.2 |
| α (degrees) | 8 | 8 | 8 |
| γ (degrees) | 136 | 130 | 130 |
| φ (degrees) | 12 | 14 | 18 |
| θ (degrees) | 18 | 15 | 13 |
| s (μm) | 13 | 29 | 20 |
| C1/A | 0.58 | 0.47 | 0.28 |
| C2/A | 0.29 | 0.56 | 0.65 |

TABLE 2

Edge surface shapes of injection needles according to Comparative Examples

|  | Comparative Example | | | | | |
| --- | --- | --- | --- | --- | --- | --- |
|  | 1 | 2 | 3 | 4 | 5 | 6 |
| Outside diameter (mm) | 0.2 | 0.2 | 0.25 | 0.25 | 0.3 | 0.3 |
| α (degrees) | 9 | 8.5 | 9 | 9 | 9 | 9 |
| γ (degrees) | 130 | 129 | 120 | 130 | 120 | 130 |
| φ (degrees) | 18 | 18 | 18 | 22 | 18 | 22 |
| θ (degrees) | 18 | 18 | 18 | 22 | 18 | 22 |
| s (μm) | 0 | 0 | 0 | 0 | 0 | 0 |
| C1/A | 0.43 | 0.36 | 0.46 | 0.34 | 0.47 | 0.34 |
| C2/A | 0.43 | 0.36 | 0.46 | 0.34 | 0.47 | 0.34 |

Figure 6:
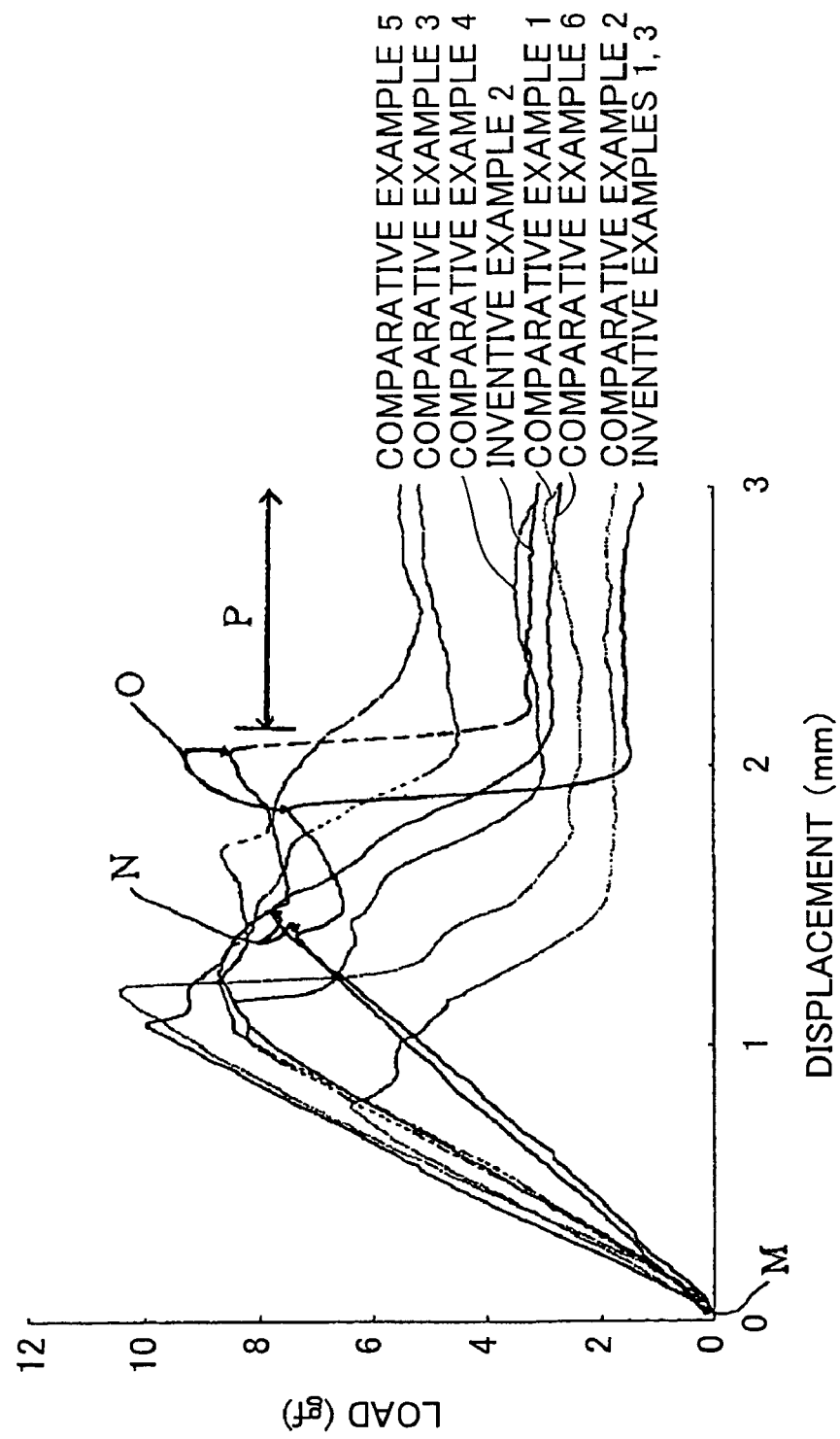
FIG. 6 is a graph showing penetration resistance curves measured in Examples.

The injection needles according to Inventive Examples 1 through 3 and Comparative Examples 1 through 6 were used to pierce a silicone rubber sheet (durometer hardness A50: JIS-K6253) having a thickness of 0.5 mm, and penetration of resistance curves were measured using an autograph (manufactured by Shimadzu Corp. AGS-1 kNG). The penetration speed was 10 mm/mm. The obtained penetration resistance curves are shown in FIG. 6. There has been no significant difference between the penetration resistance curves of Inventive Example 3 and Inventive Example 1.

As can be seen from FIG. 6, the penetration resistance curves are divided into a point M where the distal end (needle point) of the edge surface makes initial contact with the object (silicone rubber sheet) to be pierced, a point N where the needle point penetrates the object having the thickness of 0.5 mm, a point O where the entire edge surface penetrates the object, and a point P where the needle tube passes through the object. The penetration resistance curves according to the Inventive Examples indicate that the gradients of the penetration resistance curves after the distal end (needle point) of the edge surface makes initial contact with the object until the needle point penetrates the object, i.e., between the points M, N, are smaller than those of the Comparative Examples. The gradients of the penetration resistance curves are shown in Table 3.

TABLE 3

Gradients of penetration resistance curves between the points M, N

| Specimen | Gradient (gf/mm) |
| --- | --- |
| Inventive Example 1 | 5.31 |
| Inventive Example 2 | 5.13 |
| Inventive Example 3 | 5.36 |
| Comparative Example 1 | 9.76 |
| Comparative Example 2 | 8.92 |
| Comparative Example 3 | 8.35 |
| Comparative Example 4 | 8.12 |
| Comparative Example 5 | 8.10 |
| Comparative Example 6 | 9.76 |

The measured penetration resistance curves show that the injection needles according to Inventive Examples 1 through 3 have smaller gradients of penetration resistance curves between the points M, N than injection needles according to Comparative Examples 1 through 6. This indicates that when the edge surface is brought into contact with the object from its distal end and further forced into the object, forces that are applied from the edge surface to the object are sufficiently distributed. Therefore, as described above, the puncture pain caused when the injection needle penetrates the skin is reduced.

According to the Comparative Examples, penetration resistance curves were measured using injection needle having different outside diameters, and exhibited substantially the same gradients. This indicates that the gradients of the penetration resistance curves do not depend upon the diameters of the injection needles. Since the injection needle according to the present invention has the edge surface of a particular structure, i.e., a structure in which the needle point is not present on the central plane, the gradient of the penetration resistance curve between the points M, N is small. Therefore, when the edge surface is brought into contact with the object from its distal end and further forced into the object, forces that are applied from the edge surface to the object are sufficiently distributed.

INDUSTRIAL APPLICABILITY

As described above, the injection needle according to the present invention is capable of effectively distributing forces that are applied from the edge surface to the skin when the edge surface is brought into contact with the skin from its distal end and further forced into the skin. Therefore, the puncture pain that is caused to the patient when the injection needle pierces the skin can be reduced, allowing the patient to use the injection needle comfortably with ease.

The invention claimed is:

1. An injection needle having a first ground facet formed on a distal end of a needle tube and at least two ground facets subsequently formed to provide a needle point, characterized in that said first ground facet is of a substantially elliptical shape;

a plane which crosses said first ground facet perpendicularly thereto, comprises a central axis of said needle tube, and is parallel to the central axis is regarded as a central plane;

the needle point is not present on said central plane; and said needle point is the only needle point, wherein a planar surface forming said first ground facet forms an angle $\alpha$ with a central axis of said needle point, a planar surface forming said second ground facet forms an angle $\phi$ with the central axis of said needle point, and a planar surface forming said third ground facet forms an angle $\theta$ with the central axis of said needle point, and wherein a $\alpha<\phi, \alpha<\theta$, and $\phi \neq \theta$.

2. An injection needle according to claim 1, wherein the minimum distance between said needle point and said central plane is in the range from 3 to 20% of the maximum outside diameter of said first ground facet in the direction of a minor axis thereof.

3. An injection needle according to claims 1, wherein when the injection needle pierces a silicone rubber sheet having a thickness of 0.5 mm at a penetration speed of 10 mm/mm., an initial value of the load with respect to a penetration distance is 6 gf/mm or less.

4. An injection needle according to claim 1, wherein the substantially elliptical shape of the first ground facet possesses a major axis, and said needle point is not present on said major axis.

5. An injection needle according to claim 1, wherein the at least two ground facets comprise second and third ground facets each possessing a curved outer edge, the central plane intersecting a distal end region of the curved outer edge of one of the second and third ground facets.

6. An injection needle having an edge surface comprising three ground facets formed on a distal end of a needle tube to provide a needle point, characterized in that one of the ground facets which is remotest from said needle point is regarded as a first ground facet, and the other ground facets as a second ground facet and a third ground facet;

said needle point is located on a boundary between said second ground facet and said third ground facet;

an angle $\alpha$ between said first ground facet and a central axis of said needle point, an angle $\phi$ between said second ground facet and the central axis of said needle point, and an angle $\theta$ between said third ground facet and the central axis of said needle point are related to each other by: $\alpha<\phi, \alpha<\theta$, and $\phi \neq \theta$;

a plane which crosses said first ground facet perpendicularly thereto, is parallel to the central axis, and comprises the central axis of said needle tube is regarded as a central plane;

the minimum distance between said needle point and said central plane is in the range from 3 to 20% of the maximum outside diameter of said edge surface in the direction of a minor axis thereof; and said needle point is the only needle point.

7. An injection needle according to claim 6, wherein the length of said second ground facet in the direction of the central axis and the length of said third ground facet in the direction of the central axis are in the range from 20 to 80% of the whole length of the ground facets in the direction of the central axis.

8. An injection needle according to claim 6, wherein when the injection needle pierces a silicone rubber sheet having a thickness of 0.5 mm at a penetration speed of 10 mm/mm., an initial value of the load with respect to a penetration distance is 6 gf/mm or less.

9. An injection needle according to claim 6, wherein said first ground facet is of a substantially elliptical shape possessing a major axis, and said needle point is not present on said major axis.

10. An injection needle according to claim 6, wherein the second and third ground facets each possess a curved outer edge, the central plane intersecting a distal end region of the curved outer edge of one of the second and third ground facets.

11. An injection needle produced by a method comprising grinding a distal end portion of a needle tube to form a first ground facet, and grinding the first ground facet to form at least second and third ground facets which provide a needle point, the injection needle is characterized in that a plane which crosses said first ground facet perpendicularly thereto, comprises a central axis of said needle tube, and is parallel to the central axis is regarded as a central plane;

the needle point is not present on said central plane; and said needle point is the only needle point, wherein a planar surface forming said first ground facet forms an angle $\alpha$ with a central axis of said needle point, a planar surface forming said second ground facet forms an angle $\phi$ with the central axis of said needle point, and a planar surface forming said third ground facet forms an angle $\theta$ with the central axis of said needle point, and wherein $\alpha<\phi, \alpha<\theta$, and $\phi \neq \theta$.

12. An injection needle according to claim 11, wherein the minimum distance between said needle point and said central plane is in the range from 3 to 20% of the maximum outside diameter of said first ground facet in the direction of a minor axis thereof.

13. An injection needle according to claim 11, wherein when the injection needle pierces a silicone rubber sheet having a thickness of 0.5 mm at a penetration speed of 10 mm/mm., an initial value of the load with respect to a penetration distance is 6 gf/mn or less.

14. An injection needle according to claim 11, wherein said first ground facet is of a substantially elliptical shape possessing a major axis, and said needle point is not present on said major axis.

15. An injection needle according to claim 11, wherein the second and third ground facets each possess a curved outer edge, the central plane intersecting a distal end region of the curved outer edge of one of the second and third ground facets.

16. An injection needle having a first ground facet formed on a distal end of a needle tube and at least two ground facets subsequently formed to provide a needle point, characterized in that said first ground facet is of a substantially elliptical shape;

a plane which crosses said first ground facet perpendicularly thereto, comprises a central axis of said needle tube, and is parallel to the central axis is regarded as a central plane;

the needle point is not present on said central plane; and said needle point is the only needle point, wherein the at least two ground facets comprise second and third ground facets each possessing a curved outer edge, the central plane intersecting a distal end region of the curved outer edge of one of the second and third ground facets.

17. An injection needle produced by a method comprising grinding a distal end portion of a needle tube to form a first ground facet, and grinding the first ground facet to form at least second and third ground facets which provide a needle point, the injection needle is characterized in that a plane which crosses said first ground facet perpendicularly thereto, comprises a central axis of said needle tube, and is parallel to the central axis is regarded as a central plane;

the needle point is not present on said central plane; and said needle point is the only needle point, wherein the second and third ground facets each possess a curved outer edge, the central plane intersecting a distal end region of the curved outer edge of one of the second and third ground facets.

* * * * *

UNITED STATES PATENT AND TRADEMARK OFFICE
CERTIFICATE OF CORRECTION

PATENT NO.         : 7,435,239 B2
APPLICATION NO. : 10/509657
DATED              : October 14, 2008
INVENTOR(S)        : Teruyuki Yatabe et al.

It is certified that error appears in the above-identified patent and that said Letters Patent is hereby corrected as shown below:

Title Page, (30) Foreign Application Priority Data: Change "March 27, 2003" to --March 29, 2002--.

Column 9, Line 7: Change "10 mm/mm" to --10 mm/min.--

Signed and Sealed this

Twenty-fourth Day of February, 2009

JOHN DOLL
*Acting Director of the United States Patent and Trademark Office*